United States Patent [19]
Williams

[11] 4,117,835
[45] Oct. 3, 1978

[54] METHOD AND APPARATUS FOR BLOOD PRESSURE MEASUREMENTS

[75] Inventor: William J. Williams, Ann Arbor, Mich.

[73] Assignee: Weisman & Allen, Madison Heights, Mich.

[21] Appl. No.: 748,528

[22] Filed: Dec. 8, 1976

[51] Int. Cl.$^2$ .............................................. A61B 5/02
[52] U.S. Cl. ......................... 128/2.05 M; 128/2.05 A
[58] Field of Search .................... 128/2.05 M, 2.05 A, 128/2.05 R

[56] References Cited

U.S. PATENT DOCUMENTS

| | | | |
|---|---|---|---|
| 2,352,875 | 7/1944 | Williams et al. | 128/2.05 A |
| 2,710,001 | 6/1955 | Freyburger | 128/2.05 M |
| 2,865,365 | 12/1958 | Newland et al. | 128/2.05 A |
| 3,371,661 | 3/1968 | Budde | 128/2.05 M |
| 3,903,872 | 9/1975 | Link | 128/2.05 A |

*Primary Examiner*—Lee S. Cohen
*Attorney, Agent, or Firm*—Krass & Young

[57] ABSTRACT

A method and apparatus for making blood pressure measurements is disclosed particularly adapted to automated measurements of systolic and diastolic blood pressure values. The method includes detecting the rate of change of pressure values existing in an inflatable occluding cuff encircling an extremity of the subject, in whom the blood pressure measurements are to be taken, as the pressure in the occluding cuff is varied from a pressure sufficiently high to completely occlude blood flow to the extremity, to a pressure value in which blood flow takes place in the extremity substantially unaffected by the encircling inflatable cuff. The rate of change of pressure is disclosed as precipitously increasing at a cuff pressure value corresponding to a systolic blood pressure and precipitously declining at a cuff pressure corresponding to diastolic pressure, with the onset of a precipitous increase and decrease detected in order to ascertain the systolic and diastolic pressure values respectively. The particular arrangement disclosed features a rate-of-change-of- pressure transducer which produces a signal directly corresponding to the rate of change of pressure. The transducer includes a pressure responsive moveable element such as a diaphragm subjected to the varying cuff pressures, which element is drivingly connected to a magnetic core surrounded by an electrically conductive coil, the rate of movement of the magnetic core with respect to the encircling coil inducing an emf in the electrical coil corresponding to the rate of change of pressure to which the diaphragm is subjected, which signal is used to detect the systolic and diastolic cuff pressure values as described.

21 Claims, 4 Drawing Figures

METHOD AND APPARATUS FOR BLOOD PRESSURE MEASUREMENTS

BACKGROUND OF THE INVENTION

1. Field of the Invention

This invention concerns methods and arrangements for non-invasively detecting the systolic and diastolic blood pressure values, and more particularly such methods and arrangements adapted to automated determinations of such blood pressure values.

2. Description of the Prior Art

The measurement of systolic and diastolic blood pressure values in human subject for clinical and diagnostic purposes has traditionally been carried out by a doctor, nurse or other clinical technician by a procedure including inflating an occluding cuff encircling the subject's upper arm to a pressure value corresponding to that in which blood flow in the arm is occluded. The pressure in the cuff is then allowed to decline gradually to a pressure value in which blood flow can take place substantially unimpeded by the cuff. The doctor or nurse listens by means of a stethoscope for certain sounds known as the Korotkoff sounds created by the initiation of blood flow in the arterial vessels, which sounds occur characteristically at cuff pressure values corresponding to systolic and diastolic blood pressure values. By observing a manometer which monitors cuff pressures, the examiner can thus determine systolic and diastolic blood pressure values. The systolic blood pressure value is that value existing within the blood circulatory system as the point of maximum heart contraction while the diastolic blood pressure value is that blood pressure existing in the circulatory system when the heart is in its relaxed or uncontracted condition. Due to the pervasive incidence of abnormalities in blood pressure, the insidious onset of such condition, and the potentially highly destructive effects on the individuals afflicted, it has heretofore been seen as highly desirable that mass screening of potential victims be continually carried out. Such mass screening would preferably involve an automation of the blood presure measurement process to reduce the need for involvement of highly trained medical personnel.

Such automation would also be advantageous within hospitals and other medical facilities to reduce the cost of operation by minimizing the extent of services required by such highly trained individuals while it saved time providing adequate diagnostic support for such operations. Obviously, reliable and accurate results would be essential from any such apparatus. Numerous such atuomated systems have been proposed and implemented in the past, one such system being described in co-pending application ser. No. 714,097, filed on Aug. 13, 1976, entitled METHOD AND ARRANGEMENT FOR MEASURING BLOOD PRESSURE. In this system the blood pressure wave form which is the variation of pressure with time in the cuff as the cuff is cycled through an occluding-non-occluding cycle is analysed with certain characteristic changes in the wave form being established as criteria for detecting the systolic and diastolic pressure points. Other methods have involved the use of a microphone and other means for automatically detecting the presence of the so-called Korotkoff sounds.

Another approach involves the use of plethysmography to detect the blood flow conditions in the extremity downstream of the cuff with the existence of a flow or no-flow condition used to identify the systolic and diastolic pressure values.

Yet another approach involves tonometry in which a force transducer is used to directly measure the pressure existing in the arterial network directly without the need of an occluding cuff, and the maximum and minimum pressure values detected which correspond precisely to systolic and diastolic pressure values.

All these approaches are theoretically valid but each suffer from various disadvantages.

Firstly, the pressure values so obtained should correspond very closely to values which would be obtained by the exercise of traditional procedures since the body of clinical data which exists and provides a reference for forming diagnoses had been obtained by the use of these traditional procedures. For a number of reasons no automated measurement technique has heretofore provided such close correspondence.

Secondly, these techniques all involve rather sophisticated apparatus and electronic processing equipment, i.e., micro-processors or mini-computers and analyses of rather complex electronic variables, such that the results of such analyses is not highly reliable and repeatable, leading to a certain distrust of the results of such tests carried out on such apparatus. This attributes in no small part to a widespread reluctance to rely on such apparatus by the doctors and nurses responsible for such examinations.

Further, such apparatus commonly use sensitive transducers, microphones, etc. which are apt to require extensive and regular skilled maintenance, and which tend to malfunction, particularly when subject to abuse which would be the case if such apparatus was installed in public buildings, etc. for coin operated applications.

These factors, while contributing to a degree of a lack of reliability, also tends to increase the expense of manufacturing and operating such equipment.

Accordingly, it is an object of the present invention to provide a method or technique of making blood pressure measurements corresponding to the systolic and diastolic pressure values which is adapted to such automated measurements and which is inherently highly reliable.

It is another object of the present invention to provide such a method and apparatus which produces readings which closely correspond with readings taken by the traditional clinical procedures.

It is yet another object of the present invention to provide such an apparatus which is relatively simple and troublefree and requires little maintenance while at the same time producing highly repeatable results.

SUMMARY OF THE INVENTION

These and other objects which will become apparent upon a reading of the following specification and claims are accomplished by a technique in which the rate of pressure change in an applied deformable fluid pressure enclosure such as a cuff is monitored during an occluding to non-occluding pressure cycle with the onset of a precipitous increase in the rate of change of such said pressure values detected corresponding to the systolic cuff pressure value while the onset of a precipitous decline in the rate of pressure change is also detected corresponding to the diastolic pressure value. The corresponding cuff pressures are continuously monitored during such cycle and the pressure values existing at the systolic and diastolic rate of pressure change points are recorded and displayed as the systolic and diastolic pressure values respectively. The arrangement for measuring the rate of change or monitoring the rate of pressure change in the occluding cuff conists of a rate of change pressure transducer which consists of an element movable in response to changes in pressure in said cuff, with a movable magnetized core adapted to move together with the moveable element and also includes an electrically conductive coil surrounding the magnetized core so that the rate of movement of the magnetic core induces a corresponding emf in the electrically conductive coil, corresponding to the rate of pressure change in the occluding cuff. In the disclosed embodiment the onset of the precipitous increases and decrease of the rate of pressure change values is detected by a threshold detector in which rate of pressure change values which exist at given fractions of the maximum values are taken to indicate the onset of such precipitous increase and decline respectively.

DETAILED DESCRIPTION

The following detailed description certain specific terminology will be utilized for the sake of clarity and a particular embodiment described in accordance with the requirements of 35 USC 112. It is to be understood that the invention is not intended to be limited thereby, as it is indeed capable of taking many forms and variations and having many variations within the scope of the appended claims.

Figure 1:
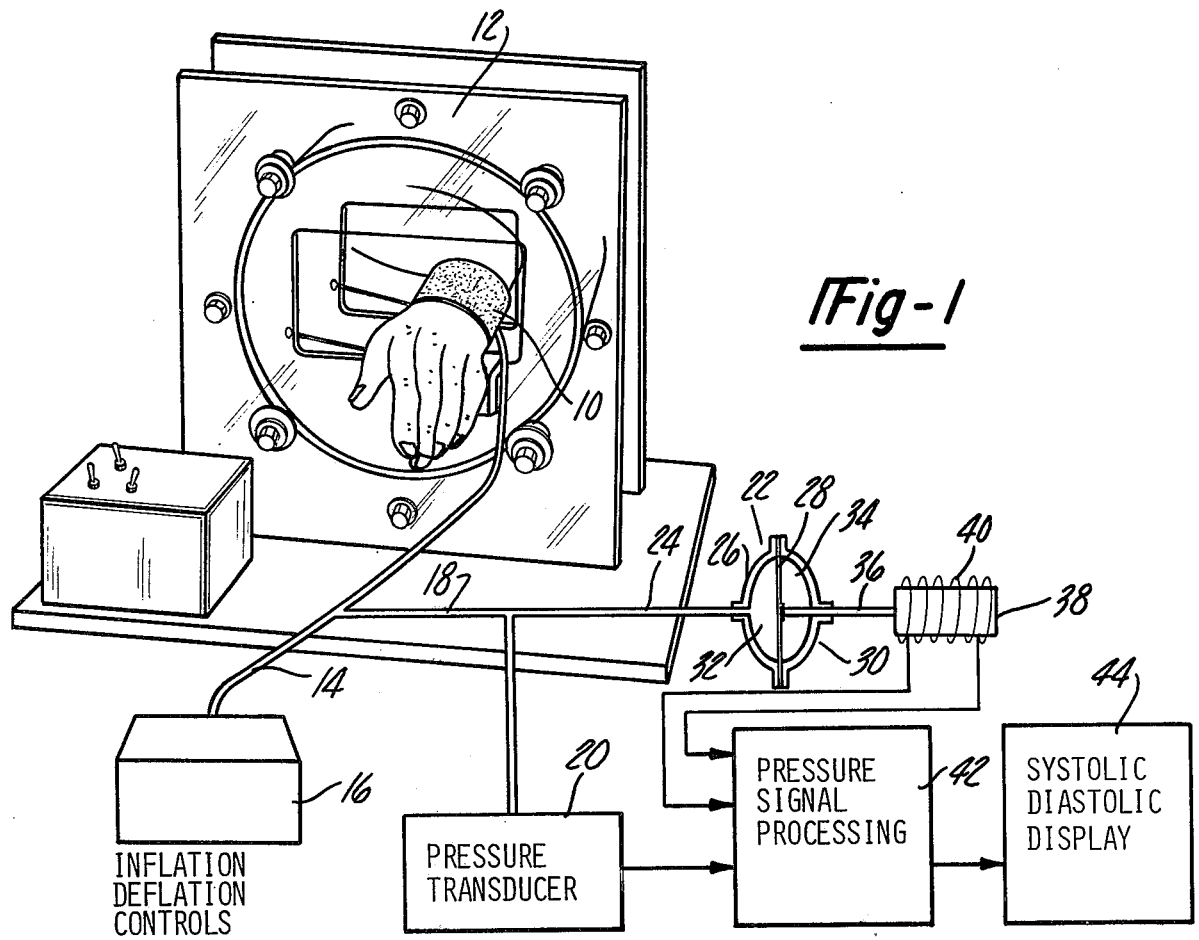
FIG. 1 is a diagramatic representation of apparatus adapted to carry out blood pressure measurements according to the method of the present invention.

Referring to the drawings, the arrangement according to the present invention includes a deformable fluid pressure enclosure such as an inflatable occluding cuff 10, adapted to be applied to an extremity of a human subject, depicted in FIG. 1 as applied to the wrist. Ideally, the cuff application would be carried out automatically in order that the entire system would be automated. In co-pending application Ser. No. 752,567, a suitable apparatus for automatically applying the blood pressure measurement inflatable cuff is disclosed and one view of which is shown in FIG. 1. This apparatus includes a rotatable drum 12 in which is disposed the inflatable occluding cuff 10, rotation of the drum 12 adapted to wind the inflatable cuff 10 about the wrist of the subject, with reverse rotation of the drum 12 causing unwinding of the cuff 10 on the wrist of the subject. The details of this apparatus are not essential for an understanding of the present invention and reference is therefore made to the above-identified pending patent application for further details of such a system.

Upon complete encirclement of the occluding cuff 10 about the wrist of the subject, an automated inflation - deflation cycling of the inflatable occluding cuff 10 takes place via a tube 14 placed in communication with a low pressure pneumatic source (not shown) under the control of inflation - deflation control system 16. After being inflated, the cuff 10 pressure is then controllably deflated over a period of time on the order of 20 seconds. The initial pressure is selected to be above that corresponding to systolic such that complete occlusion of the arteries would take place and thence the pressure is reduced at a controlled rate to a point where the cuff 10 has no appreciable effect on blood flow in the encircled limb. Since such systems, typically including solenoid valves, pressure sensors, etc., are well known in the state of the art at present, the details of the same are not here included.

An example of such a system is set forth in detail, in co-pending application Ser. No. 714,097, filed Aug. 13, 1976.

The pressure conditions existing within the cuff 10 during such cycling of the pressure from that above systolic to that below diastolic is sensed by a pressure tap 18 in fluid communication with the fluid tube 14. The pressure conditions monitored includes the sensing of the gross pressure, that is, the pressure condition existing as a function of time in the inflatable occluding cuff 10. This is done by means of a pressure transducer 20 of conventional design, having response characteristics such as to accurately monitor the pressure fluctuations existing during the inflation - deflation cycle, as well as the fluctuations induced by the interaction of the subject's pulse with the inflatable cuff 10. The pressure transducer 20 thus provides means for generating a signal corresponding to the pressure value existing within the inflatable occluding cuff 10.

At the same time an arrangement is provided, indicated at 22 which comprises a means of directly measuring the rate of change of the pressure in the inflatable cuff 10 by virtue of a brand tap 24 in communication with a diaphragm assembly 26 which includes a flexible diaphragm 28, dividing a housing 30 into respective compartments, with compartment 32 in fluid communication with the inflatable cuff 10 via branch tap conduit 24 and wherein compartment 34 is either vented to atmosphere or subjected to some other reference pressure being exerted therein. The diaphragm 28 is drivingly connected to a rod 36 so that movements of the diaphragm 28 in response to changed pressure conditions in the compartment 32 (corresponding to changes in pressure in the inflatable cuff 10) produce corresponding movements of the rod 36. The rod 36 in turn is affixed to a magnetic core element 38 which is disposed within the interior of an electrically conductive coil 40. The position of the magnetic core 38 thus corresponds to the pressure contained in the compartment 32, in turn corresponding to the pressure in the inflatable cuff 10, such that displacement of the magnetic core 38 corresponds to changes in pressure in inflatable cuff 10, with the relative rate of change of displacement of magnetic core 38 inducing a corresponding electromotive force in the conductive coil 40, in accordance with well known principles of electromagnetics. This arrangement thus provides a means for generating directly a signal corresponding to the rate of change of pressure in the inflatable cuff 10.

This signal is transmitted to a pressure signal processing arrangement 42 which likewise receives the gross pressure transducer 20 signals for analysis, by which analysis the systolic and diastolic pressure values are generated which are then displayed in a systolic - diastolic display 44. The systolic and diastolic pressure values are determined by an analysis of the rate of change of pressure values existing in the inflatable cuff during the inflation - deflation cycle.

The validity of this approach can be appreciated by the following analysis of the physical relationship between the encircled body member and the inflatable cuff.

Consider the encircled body limb as a distensible fluid pressure vessel, to which has been applied a deformable fluid pressure enclosure (the inflatable cuff 10) which is pressurized. If the pressure in the fluid pressure enclosure is greater than the maximum pressure which will be experienced in the encircled distensible fluid vessel, pressure pulsations in the distensible fluid vessel will have substantially no effect on the pressure in the surrounding fluid pressure enclosure. Thus, if the pressure in the surrounding fluid pressure enclosure is initially greater than that in the distensible fluid vessel, and is gradually reduced at a steady rate, the rate of change of pressure would be substantially constant.

Upon decline of the pressure in the surrounding fluid pressure enclosure to a level approximately equal to the maximum pressure pulsations in the distensible fluid pressure vessel, the pressure pulsations therein would begin to cause a variation in the pressure in the surrounding fluid pressure enclosure, since physical distension of the fluid pressure vessel can then cause a reduction in the volume of the surrounding fluid pressure enclosure, causing a corresponding increase in pressure and also a reduction in pressure upon returning of the distensible fluid pressure vessel to the initial condition. At this point the rate of change of pressure in the surrounding fluid pressure enclosure shows a precipitous increase as the interaction described begins to show its effect, particularly where this interaction augments the steady pressure decline. Similarly, as the pressure in the surrounding fluid pressure enclosure declines to a point below that of the minimum pressure experienced in the distensible fluid pressure vessel, the pulsations will no longer produce appreciable distention of the elastically distensible fluid pressure vessel since the pressure exerted by the surrounding fluid pressure enclosure no longer has an effect, i.e., the fluid pressure vessel will simply remain fully open.

At this point there will be a precipitous decline in the rate of change of pressure values inasmuch as only the controlled or steady pressure decline will then exist.

Accordingly, by detecting the onset of the precipitous increase and decrease of the rate of change of pressure values over the course of the inflation - deflation cycle, while at the same time monitoring of the gross pressure values, identification of the gross pressure values at systolic and diastolic pressure values points will yield in turn the systolic and diastolic pressure values.

While this rate of change of pressure function could be produced by differentiation electronically or otherwise, the direct generation of a signal corresponding to this parameter offers great advantages, since the low signal-to-noise ratio of the gross pressure signals may render electronic differentiation extremely difficult and inaccurate. Accordingly, the arrangement 22 is utilized in the present preferred embodiment.

Figure 2:
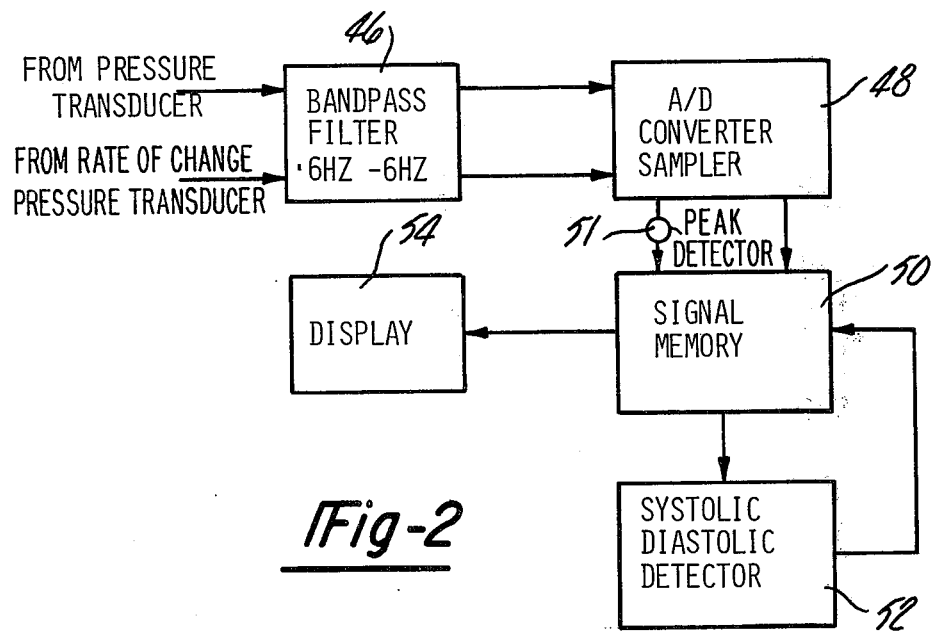
FIG. 2 is a block diagram representation of the signal processing system according to the present invention.

Referring to FIG. 2 a simple block diagram of the scheme described is set forth. A band pass filter 46 is provided to minimize spurious signals created by the effect of noise, gross movements of the subject, etc. For these purposes a pass range of 0.6 hertz to 6.0 hertz can advantageously be used. The lower end, 0.6 hertz, eliminates the gradual or steady state signals, such as the gross arm movements as noted, while the upper end of the frequency range, 6.0 hertz, allows transmission of the heart beat pulsations to the 6th harmonic, since this is approximately 6 times the frequency of the normal heart beat, thereby eliminating to the maximum extent extraneous signals, while passing all true signals. From the band pass filter, the signals are transmitted to an A/D converter 48 which converts the analog signals from the pressure transducer 20 and the rate of change of pressure transducer 22 into digital signals, and samples them at a high rate relative to the frequency of the heart beat, i.e., 1,000 times per second. The digitized pressure signals are sampled and held in a signal memory 50, while the rate of pressure change is transmitted to a peak detector 51 which detects the peakings of the rate of change of pressure signal values over the period of the inflation - deflation cycle and holds them in the signal memory 50, together with the pressure signal values. From these peak signal values of the rate of pressure change, a detector arrangement 52 analyses the peakings of the rate of pressure change signal values and determines the point in time of the cuff pressurization cycle at which the systolic and diastolic pressures were achieved within the inflatable cuff 10.

Upon making such a determination, the pressure transducer signal existing at that time is selected from the signal memory 50 and the corresponding pressure values are then transmitted to a display 54.

Figure 3:
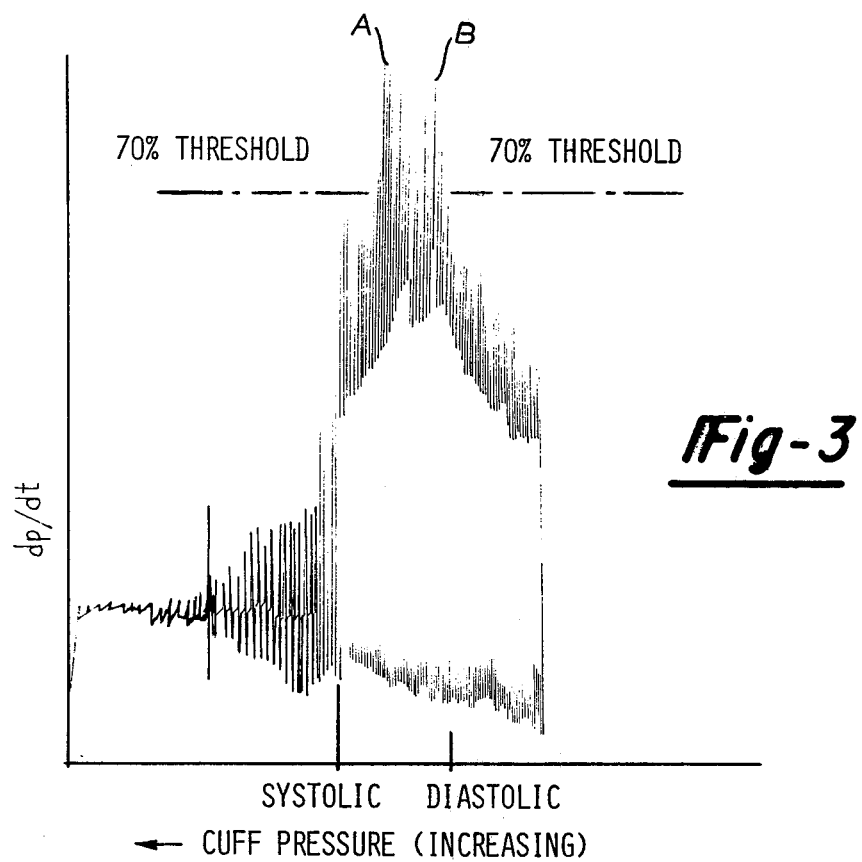
FIG. 3 is a plot of the variations in the rate of change of pressure, as the pressure in an occluding cuff is varied from a maximum value at which the cuff completely occludes blood flow to a pressure value substantially below that corresponding to diastolic blood pressure.

The nature of the systolic - diastolic detection can be more fully understood by reference to FIG. 3, which is a typical tracing obtained of the variations in the rate of change of pressure, $dp/dt$, versus gross pressure, with maximum pressure declining from the lefthand side of the curve, reducing to the right. As was developed above, as the pressure in the cuff 10 declines to a point where the distension of the blood vessel, caused by the initiation of blood flow, begins to create pressure surges in the cuff 10, the rate of change of pressure sensed will be at a maximum as indicated at peak A. This condition of high peak values will continue until the pressure drops below diastolic as indicated at point B. However, the onset of the precipitous increase and decrease respectively are where the systolic and diastolic pressure values exist, i.e., at the point where the arterial flow just begins and at that point where the blood vessels are fully distended. For this reason it is not possible to simply take the two peak values, A and B, and determine the corresponding gross pressures to establish systolic and diastolic pressure, respectively, but the detection of the onset of the increase and decrease respectively must be established.

One such arrangement for determining these points includes a threshold signal analysis in which the peak rate of change of pressure values, A and B, would be determined after the sampling of the rate of pressure values during the course of inflation - deflation cycle and then a 70% threshold factor (as indicated in FIG. 3) applied to the rate of change of pressure signal A and the peak rate of change of pressure peak most closely corresponding to said threshold would be determined by a survey of the contents of signal memory 50 and the gross pressure signals value existing at this point in time would then be taken as systolic and displayed in the display 54.

Similarly for the maximum pressure rating B, subsequent to the maximum pressure reading A, 70% of this rate of change of the pressure signal value would be determined as the appropriate signal and the signal memory 50 then surveyed to determine the rate of change of pressure signal value most closely corresponding to this signal value and in turn corresponding gross pressure signal value existing at that point in time would then be taken as the diastolic pressure and displayed in the display 54.

Figure 4:
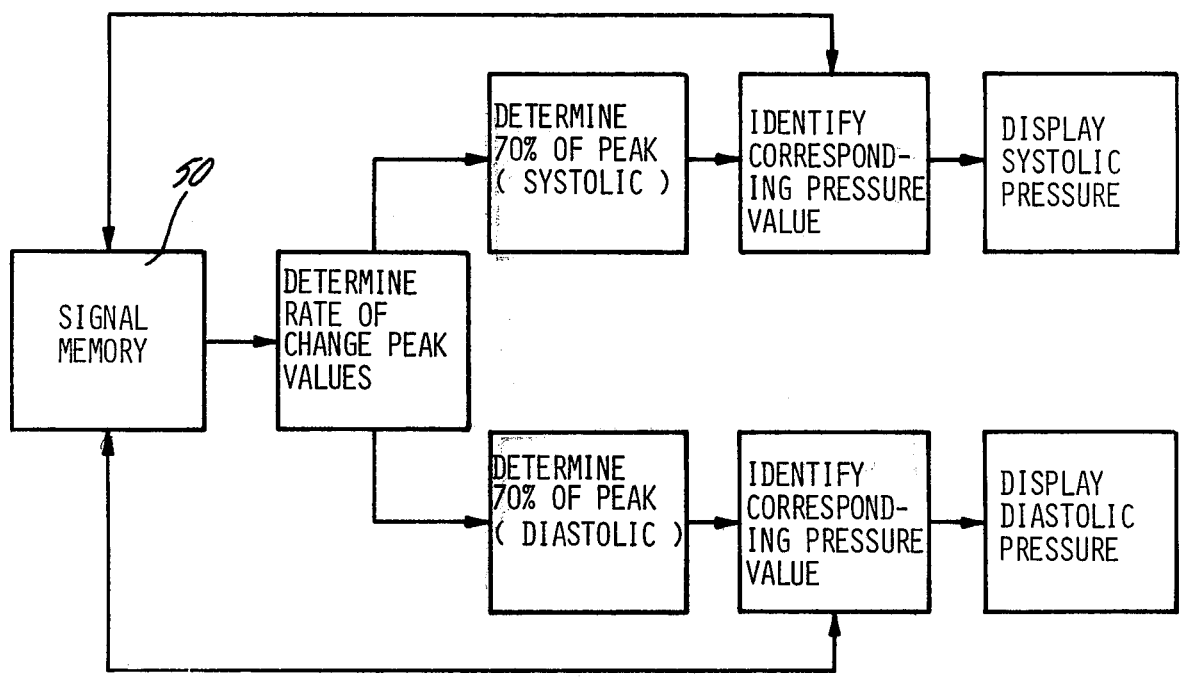
FIG. 4 is a block diagram representation of a method of detecting the systolic and diastolic pressure values from the rate of change of pressure values measured in the course of a pressurization cycle of an occluding cuff.

FIG. 4 is a block diagram representation of an implementation of such a detection scheme. The rate of change of pressure peaks stored in the signal memory 50 would be surveyed to determine the peak values among these rate of change of pressure signal peaks. In one branch there would be a determination of the magnitude of 70% of that signal value, corresponding to A. Next, the rate of change of pressure signal values most closely corresponding to the 70% value would be located in the signal memory 50. Next, the corresponding gross pressure signal reading most closely corresponding to the 70% of peak signal value would be determined with this signal value then being taken as systolic and displayed as shown. Similarly, the rate of change peak values would be corresponding to the B peak point would be multiplied by 0.70 and a subsequent identification of the corresponding rate of change of pressure value peaks determined and contained in the signal memory 50 and the gross pressure value corresponding thereto then established by similar survey and this pressure being taken as diastolic and displayed as such as shown.

The precise threshold value for a given design of the various parts of the system would be determined by analysis of a representative sample of traces obtained from the particular equipment used.

Other approaches are, of course, possible such as a detection of the point of inflection, upwardly and downwardly, of the curve defined by the envelope of the rate of change of pressure peak values in order to detect the onset of precipitous increases and precipitous decreases of rate of change of pressure signal values. It should be appreciated from the foregoing that the objects of the present invention have been accomplished by this approach to the systolic - diastolic pressure detection scheme since the detection mode is considerably simpler and more reliable and less subject to error than the above-described prior art methods. Particularly is this so when the direct obtaining of the rate of change of pressure signal values is carried out by virtue of a rate of pressure change transducing arrangement disclosed since the problem of noise, etc. in a differentiated signal is thereby obviated further contributing to the accuracy and simplicity and reliability of the system. It should be understood, of course, that many variations in the specifics disclosed are possible since, for example, the gross pressure transducer signals could be differentiated in given instances if the use of a direct rate of pressure change transducer were eliminated. Many variations in the analytic techniques of the rate of pressure change signal values can be made, since the systolic and diastolic pressure point values are rather easily established by reference to this function.

The variations in the shape of the plots derived by the apparatus of the present invention indicates differences between two individuals. For example, let's take two individuals with the same systolic and diastolic blood pressure. While this apparatus will determine those pressures, the curves for these two individuals may have substantial differences and those differences are diagnostic of differences in the cardiovascular systems of the two individuals. In particular this information is related to hypertrophy in various chambers of the heart, alterations in the conductive mechanism intrinsic to the heart, and changes in flow dynamics in the peripheral system.

The embodiments of the invention in which an exclusive property or privilege is claimed are defined as follows:

1. A method of determining the systolic and diastolic blood pressure of a subject, including the steps of: applying a deformable fluid pressure enclosure to an extremity of the subject; varying the pressure in said deformable fluid pressure enclosure between a maximum pressure value corresponding to that required to completely occlude the blood pressure vessels of the subject in the extremity to which the fluid pressure enclosure is applied and a minimum pressure value less than that at which significant occlusion of the blood vessels occurs; monitoring the pressure existing in said deformable fluid pressure enclosure over the cycle between said maximum pressure and said minimum pressure and generating signals corresponding thereto; storing said signals in a signal memory; monitoring the rate of change of pressure in said deformable fluid pressure enclosure over said cycle and generating signals corresponding thereto; detecting the onset of precipitous increase and decrease in said rate of pressure change signals during said variation in pressure; determining systolic and diastolic pressure from said detecting step, including the step of ascertaining the respective pressure signals existing at said onset of precipitous increase and decrease respectively of rate of pressure change signals; whereby said systolic and diastolic pressure may be obtained.

2. The method according to claim 1 wherein in said step of monitoring the rate of pressure change in said deformable fluid enclosure during said variation in pressure, a rate of pressure change transducer is utilized and signals corresponding thereto are generated directly therewith.

3. The method according to claim 1 wherein in said step of detecting said onset of precipitous increase and decrease in said rate of pressure change signals, the peaks of said rate of change of pressure signals occurring over the course of said variation in pressure are detected.

4. The method according to claim 3 wherein in said step of detecting said onset of precipitous increase and decrease in said rate of pressure change signals, the maximum value of said peaks of said rate of change of pressure signals are detected.

5. The method according to claim 4 wherein in said step of detecting said onset of precipitous increase and decrease in said rate of pressure change signals, a threshold value is applied to said maximum values of said rate of pressure change signal peaks, and in said step of determining systolic and diastolic pressure, the corresponding enclosure pressure signals are determined at the rate of pressure change signals at a threshold percentage to establish said corresponding systolic and diastolic pressures.

6. The method according to claim 1 wherein in said step of applying a deformable fluid pressure enclosure to an extremity of the subject an inflatable cuff is encircled about the subject's extremity and a fluid pressure developed in said inflatable cuff of a sufficient magnitude to completely occlude blood flow in said extremity.

7. The method according to claim 6 wherein said inflatable cuff is applied about the wrist of the subject.

8. The method according to claim 1 wherein in said step of monitoring the rate of pressure change signals, a magnetic core element is caused to be displaced by variations of pressure within said deformable fluid pressure enclosure, and further including the step of surrounding said magnetic core element with an electrically conductive coil, whereby electromotive forces are induced in said coil of a magnitude corresponding to the rate of change of said displacement of said magnetic core element whereby said rate of pressure change signals are obtained from the magnitude of said electromotive forces.

9. An arrangement for determination of systolic and diastolic blood pressure values in a subject comprising means for applying a deformable fluid pressure enclosure to a body portion of a subject; inflation-deflation control means for developing a varying fluid pressure in said deformable fluid pressure enclosure of a magnitude in excess of that fluid pressure required to occlude blood flow in said body portion, and varying said pressure to a level whereat said blood flow may occur in said body portion substantially unaffected by said deformable fluid pressure enclosure; pressure transducer means monitoring the fluid pressure existing in said deformable fluid pressure enclosure during said varying of said fluid pressure applied thereto and generating corresponding pressure signals; rate of pressure change means for monitoring the rate of pressure changes occurring in said deformable fluid pressure enclosure during said fluid pressure variation and generating corresponding rate of pressure change signals; means for analyzing said rate of pressure change signals to determine the points in time at which systolic and diastolic pressure exists in said deformable fluid pressure enclosure; means for determining the corresponding pressure signals existing in said deformable fluid pressure enclosure at said points in time whereat said systolic and diastolic pressure exists, whereby said systolic and diastolic pressures are determined by said means for analyzing said rate of pressure change signals.

10. The arrangement according to claim 9 wherein said means analyzing said rate of pressure change signals comprises means determining the onset of precipitous increase and decrease in said signals to determine the points at which systolic and diastolic pressure exists respectively in said deformable fluid pressure enclosure.

11. The arrangement according to claim 10 wherein said means for determining said onset of precipitous increase and decrease in said rate of pressure change signals includes means detecting the peaks of said rate of change of pressure signals occurring over the course of said variation in pressure.

12. The arrangement according to claim 11 wherein in said means for detecting said peaks in said rate of pressure change signals, the maximum value of said peaks of said rate of change of pressure signals are determined.

13. The arrangement according to claim 12 wherein said means for determining said onset of precipitous increase and decrease in said rate of pressure change signals includes means generating a threshold percentage applied to said maximum values of said rate of pressure change signal peaks and including means for determining the corresponding pressure signals to determine said corresponding systolic and diastolic pressure values.

14. The arrangement according to claim 13 wherein said means generating a threshold percentage applied to said maximum values of said rate of pressure change signal peaks comprises means for detecting said pressure signals corresponding to 70% of said maximum rate of pressure change signals and determining the rate of pressure change signal equal to the 70% threshold when said rate of pressure change signals are decreasing in each pressure variation cycle, said corresponding pressure signals at said 70% of peak corresponding to said systolic pressure.

15. The arrangement according to claim 13 wherein said means generating a threshold value applied to said maximum values of said rate of pressure change signal peaks includes means for applying a 70% factor to said rate of pressure change signal peaks and detecting the rate of pressure change signal equal to said 70% factor in each pressure variation cycle when said rate of pressure change signals are increasing and determining the corresponding pressure signal, whereby said diastolic pressure is determined.

16. The arrangement according to claim 10 wherein said means for applying a deformable fluid pressure enclosure to a body portion of the subject includes means encircling an inflatable cuff about the subject's body portion.

17. The arrangement according to claim 16 wherein said inflatable cuff is of a size so as to be applied about the wrist of the subject.

18. The arrangement according to claim 9 wherein said rate of pressure change means comprises a movable element; means for causing movement of said element in response to variations in pressure in said deformable fluid pressure enclosure; means for measuring the rate of movement of said movable element in response to variations in pressure in said deformable fluid pressure enclosure; means for generating signals corresponding to said rate of movement of said movable element whereby signals corresponding to said rate of pressure change are generated.

19. The arrangement according to claim 18 wherein said movable element comprises a magnetic core and wherein said means for measuring the rate of movement of said movable element comprises an electrically conductive coil surrounding said magnetic core, whereby the emf induced by movement of said magnetic core corresponds to said rate of movement of said core to thereby generate said signals corresponding to movement of said movable element corresponding to the rate of pressure change in said deformable fluid pressure enclosure.

20. The arrangement according to claim 19 wherein said means for moving said movable element comprises a housing subjected to fluid pressure developed in said deformable fluid pressure enclosure including a diaphragm element and means drivingly connecting said magnetic core to said diaphragm element whereby said magnetic core moves in accordance with variations in pressures in said housing.

21. An arrangement for determination of diastolic blood pressure values in a subject comprising means for applying a deformable fluid pressure enclosure to a body portion of a subject; inflation-deflation control means for developing a varying fluid pressure in said deformable fluid pressure enclosure of a magnitude in excess of that fluid pressure required to occlude blood flow in said body portion and varying said pressure to a level whereat said blood flow may occur in said body portion substantially unaffected by said deformable fluid pressure enclosure; pressure transducer means monitoring the fluid pressure existing in said deformable fluid pressure enclosure during said varying of said fluid pressure applied thereto and generating corresponding pressure signals; rate of pressure change transducer means for monitoring the rate of pressure changes occurring in said deformable fluid pressure enclosure during said fluid pressure variation and generating corresponding rate of pressure change signals; means for analyzing said rate of pressure change signals to determine the point in time at which diastolic pressure exists in said deformable fluid pressure enclosure; means for determining the corresponding pressure signal existing in said deformable fluid pressure enclosure at said point in time whereat said diastolic pressure exists, whereby said diastolic pressure is determined by said means for analyzing said rate of pressure change signals.

* * * * *